United States Patent
Buizza et al.

(10) Patent No.: US 12,109,014 B2
(45) Date of Patent: Oct. 8, 2024

(54) SYSTEM AND METHOD FOR METABOLIC MEASUREMENTS

(71) Applicant: KONINKLIJKE PHILIPS N.V., Eindhoven (NL)

(72) Inventors: Roberto Buizza, Malden, MA (US); Francesco Vicario, Boston, MA (US)

(73) Assignee: Koninklijke Philips N.V., Eindhoven (NL)

(*) Notice: Subject to any disclaimer, the term of this patent is extended or adjusted under 35 U.S.C. 154(b) by 1057 days.

(21) Appl. No.: 17/023,483

(22) Filed: Sep. 17, 2020

(65) Prior Publication Data

US 2021/0177301 A1    Jun. 17, 2021

Related U.S. Application Data

(60) Provisional application No. 62/947,350, filed on Dec. 12, 2019.

(51) Int. Cl.
    *A61B 5/083*      (2006.01)
    *A61B 5/00*      (2006.01)

(52) U.S. Cl.
    CPC .......... *A61B 5/0836* (2013.01); *A61B 5/0833* (2013.01); *A61B 5/72* (2013.01); *A61B 2562/02* (2013.01)

(58) Field of Classification Search
CPC ... A61B 2562/02; A61B 5/083; A61B 5/0836; A61B 5/72
See application file for complete search history.

(56) References Cited

U.S. PATENT DOCUMENTS

| | | | |
|---|---|---|---|
| 5,611,348 A * | 3/1997 | Merilainen | A61B 5/083 73/23.3 |
| 6,997,880 B2 * | 2/2006 | Carlebach | A61B 5/0836 600/311 |
| 8,197,417 B2 | 6/2012 | Grimes et al. | |
| 2008/0161710 A1 | 7/2008 | Gunneson | |
| 2010/0036272 A1 | 2/2010 | Alderete et al. | |
| 2014/0336523 A1 * | 11/2014 | Brix | A61M 16/00 600/531 |
| 2017/0112413 A1 * | 4/2017 | Brugnoli | A61B 5/0833 |
| 2021/0169370 A1 * | 6/2021 | Vicario | A61B 5/6819 |

FOREIGN PATENT DOCUMENTS

WO      2019074922 A1      4/2019

\* cited by examiner

*Primary Examiner* — Eric J Messersmith
(74) *Attorney, Agent, or Firm* — Daniel H. Brean

(57) ABSTRACT

The present disclosure pertains to a system for metabolic measurements, the system comprising: a metabolic monitor configured to determine first concentration measurements of O2 and CO2 in a portion of gas exhaled by a subject during one or more breaths; and determine a first rate of O2 consumption (VO2) and a first CO2 volume production (VCO2) of the subject during the one or more breaths based on the determined first O2 concentration and the determined first CO2 concentration; a CO2 monitor configured to determine second CO2 concentration measurements in the exhaled gas during the one or more breaths; and determine second CO2 volume production (VCO2) of the subject based on the measured second CO2 concentration; and processors configured to determine a correction factor based on the determined first VCO2 and the second VCO2; and determine a corrected first VO2 using the correction factor and the first VO2.

23 Claims, 6 Drawing Sheets

SYSTEM AND METHOD FOR METABOLIC MEASUREMENTS

CROSS-REFERENCE TO RELATED APPLICATIONS

This patent application claims the priority benefit under 35 U.S.C. § 119(e) of U.S. Provisional Application No. 62/947,350 filed on Dec. 12, 2019, the contents of which are herein incorporated by reference.

BACKGROUND

1. Field

The present disclosure pertains to a system and method for metabolic measurements.

2. Description of the Related Art

Metabolic monitoring devices are generally used to assess energy expenditure of specific subjects. However, such systems maybe bulky and/or lack accuracy. Increase of energy deficit (e.g., during ICU stay) may increase morbidity, and overfeeding may lead to hyperglycemia, high carbon dioxide production (with possible deleterious effects in subjects with impaired respiratory function or respiratory failure), dyslipidemia, and/or hepatic steatosis. The present disclosure overcomes deficiencies in prior art systems.

SUMMARY

Accordingly, one or more aspects of the present disclosure relate to a system The present disclosure pertains to a system for metabolic measurements, the system comprising: a metabolic monitor configured to: determine first concentration measurements of O2 and CO2 in a portion of gas exhaled by the subject during the one or more breaths; and determine a first rate of O2 consumption (VO2) and a first CO2 volume production (VCO2) of the subject during the one or more breaths based on the determined first O2 concentration in the portion of the exhaled gas and the determined first CO2 concentration in the portion of the exhaled gas; a CO2 monitor configured to: determine second CO2 concentration measurements in the gas exhaled by the subject during the one or more breaths; and determine second CO2 volume production (VCO2) of the subject during the one or more breaths based on the measured second CO2 concentration; and one or more physical computer processors operatively connected with the plurality of sensors, the metabolic monitor, and the CO2 monitor, the one or more physical computer processors configured by computer readable instructions to: determine a correction factor based on the determined first VCO2 and the second VCO2; and determine a corrected first VO2 using the correction factor and the first VO2.

Another aspect of the present disclosure relates to a method the method comprising: determining, with a metabolic monitor, first concentration measurements of O2 and CO2 in a portion of gas exhaled by the subject during one or more breaths; determining, with the metabolic monitor, a first rate of O2 consumption (VO2) and a first CO2 volume production (VCO2) of the subject during the one or more breaths based on the determined first O2 concentration in the portion of the exhaled gas and the determined first CO2 concentration in the portion of the exhaled gas; determining, with a CO2 monitor, second CO2 concentration measurements in the gas exhaled by the subject during the one or more breaths; determining, with the CO2 monitor, second CO2 volume production (VCO2) of the subject during the one or more breaths based on the measured second CO2 concentration; determining, with one or more physical computer processors, a correction factor based on the determined first VCO2 and the second VCO2; and determining, with one or more physical computer processors a corrected first VO2 using the correction factor and the first VO2.

Still another aspect of the present disclosure relates to a system for metabolic measurements. The system comprises: means for determining first concentration measurements of O2 and CO2 in a portion of gas exhaled by the subject during one or more breaths; means for determining a first rate of O2 consumption (VO2) and a first CO2 volume production (VCO2) of the subject during the one or more breaths based on the determined first O2 concentration in the portion of the exhaled gas and the determined first CO2 concentration in the portion of the exhaled gas; means for determining second CO2 concentration measurements in the gas exhaled by the subject during the one or more breaths; means for determining second CO2 volume production (VCO2) of the subject during the one or more breaths based on the measured second CO2 concentration; means for determining a correction factor based on the determined first VCO2 and the second VCO2; and means for determining a corrected first VO2 using the correction factor and the first VO2.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
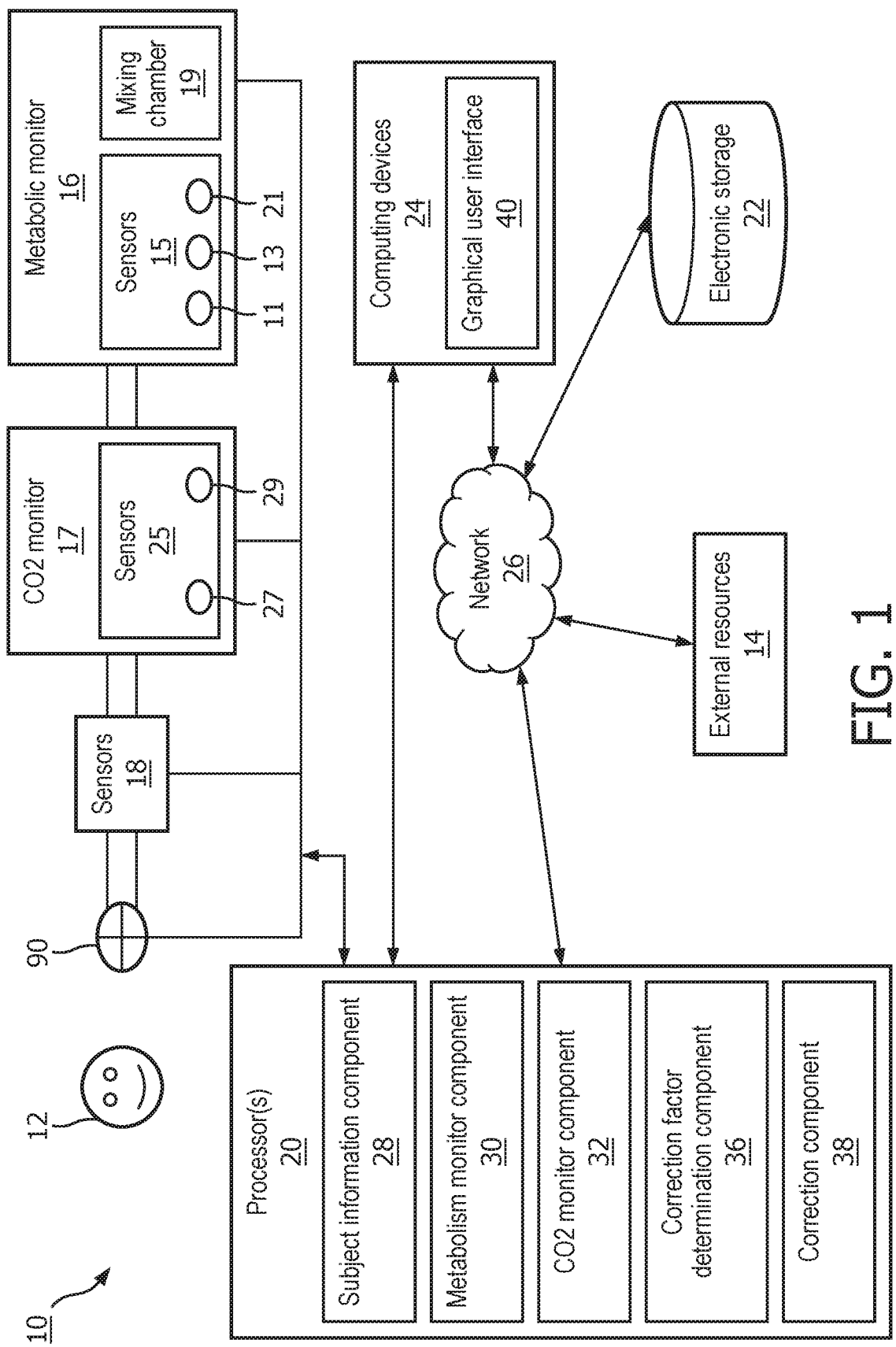
FIG. 1 is a schematic illustration of a system configured to determine metabolic measurements, in accordance with one or more embodiments.

As used herein, the singular form of "a," "an," and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In clinical practice, (e.g., in the intensive care unit (ICU)), patients commonly fail to receive adequate calories. In general, excessive hypocaloric or hypercaloric feeding should be avoided. Specifically, increase of energy deficit, during ICU stay, increases morbidity and overfeeding can lead to hyperglycemia, high carbon dioxide production (with possible deleterious effects in patients with impaired respiratory function or respiratory failure), dyslipidemia, and/or hepatic steatosis. Currently used methods assess the patient's specific energy expenditure using expensive and bulky metabolic monitoring device. In general, a metabolic monitoring device has a mixing chamber where the air from the patient is analyzed in terms of carbon dioxide and oxygen concentration in order to estimate the carbon dioxide production (VCO2), the oxygen consumption (VO2) and consequently the metabolic demand for that particular patient. In some embodiments, the oxygen consumption may be determined as a O2 volume consumption, and/or O2 mass consumption. Estimation of the oxygen consumption may require more time to have reliable measurements because of the sensors used in the bulky mixing chamber. In order to estimate the carbon dioxide produced by the patient, CO2 monitors (e.g., capnography) are generally used.

Smaller metabolic monitors with smaller mixing chamber may exist. They are able to have smaller mixing chamber because they continuously sample a percentage of the flow of the breath. However, measurements from these monitors may be inaccurate due to the proportional flow sampling (it may be difficult to sample an accurate fixed percentage of the flow when the flow is not constant as it is during a breath). In general, at higher flow the real sampling exceeds the designed value and at lower flow the real sampling falls below it. As a result of this inaccuracy, the mixing chamber will sample more gases in the initial phase of the breath where the flow is at the maximum. This portion of the breath is the one with higher concentration of carbon dioxide. This inaccuracy in the sampling may generate a higher CO2 concentration in the mixing chamber and consequently a higher CO2 production computation. The same may be true in the oxygen consumption computation.

System 10 (described in FIG. 1) may overcome the shortcomings of existing systems. System 10 takes advantage of the reliability and accuracy of measurement of VCO2 from CO2 monitors which is not impacted from the proportional sampling problem because it is a measurement performed on the entire flow. In some embodiments, such CO2 monitors may include capnographs which monitor the concentration or partial pressure of carbon dioxide (CO2) in the respiratory gases. This measurement in conjunction with the flow measurement is used to compute the carbon dioxide produced by the patient. CO2 monitors (e.g., Capnographs) do not measure O2 concentration and O2 consumption from the patient. System 10 uses the VCO2 measurement from the CO2 monitors to enhance the metabolic monitor measurement. Particularly, System 10 is configured to compute a correction factor using the VCO2 measurements from the CO2 monitors and the VCO2 measurement from a metabolic monitor and apply this correction factor to the VO2 consumption computation from the metabolic monitor. This correction factor may be applied to the VO2 measurement from the metabolic monitor. This correction allows for improving the accuracy of the vital sign VO2 needed to understand the metabolic demand of the patient.

In some embodiments, system 10 comprises one or more of metabolic monitor 16, CO2 monitor 17, sensor(s) 18, a processor 20, electronic storage 22, client computing platform(s) 24, a network 26, and/or other components. In FIG. 1, metabolic monitor 16, CO2 monitor 17, sensor(s) 18, processor 20, electronic storage 22, and client computing platform(s) 24 are shown as separate entities. In some embodiments, some and/or all of the components of system 10 and/or other components may be grouped into one or more singular devices (e.g., a user device, a metabolism monitor, a CO2 monitor, a medical device, etc.). In some embodiments, some or all components of system 10 may be co-located in a same housing and communicate directly with each other and with the subject. In some embodiments, metabolic monitor 16, CO2 monitor 17, sensor(s) 18, processor 20, and other components of system 10 may communicate with one another via wired or wireless connections. In some embodiments, system 10 may include a subject interface 90 configured to provide breathable gas to the subject and/or collect exhaled gas from the subject. In some embodiments subject interface 90 is configured to connect with other component within or outside system 10 (e.g., metabolic monitor 16, CO2 monitor, sensors, or other components, etc.). In some embodiments, the subject interface may be included in metabolic monitor 16 and/or CO2 monitor 17.

Metabolic monitor 16 is configured to provide information about the metabolic status of the subject. In some embodiments, metabolic monitor 16 is configured to determine first concentration measurements of O2 and CO2 in a portion of gas exhaled by the subject during the one or more breaths. In some embodiments, metabolic monitor 16 may include one or more sensors (15) configured to output signals related to one or more gas parameters in inhaled and/or exhaled gas by the subject. In some embodiments, sensors (15) may include one or more O2 concentration sensors (13) configured to output signals related to O2 concentration in gas inhaled and/or exhaled by the subject. In some embodiments, sensor(s) 15 include one or more CO2 concentration sensors (11) configured to output signals related to CO2 concentration in gas exhaled and/or inhaled by the subject (e.g., nondispersive infrared (NDIR) CO2 sensors). In some embodiments, sensors (15) may include a flow rate sensor (21) configured to output signals related to flow rate of inhaled and/or exhaled gas by the subject. In some embodiments, metabolic monitor (16) may include other sensors (e.g., sensors 18 described below). In some embodiments, metabolic monitor (16) comprises a mixing chamber (19) configured to collect all or a portion of the exhaled gas. In some embodiments, all exhaled gas goes to the mixing chamber where O2 and CO2 measurements are carried out. In some embodiments, a proportional sample of the exhaled gas (i.e., a fixed percentage of the overall flow at any moment in time) goes to the mixing chamber, the rest goes directly to the ambient.

In some embodiments, metabolic monitor 16 may be configured to determine a first rate of O2 consumption (VO2) and a first CO2 volume production (VCO2) of the subject during the one or more breaths. In some embodiments, the VO2 and/or VCO2 determination may be based on the determined first O2 concentration in the portion of the exhaled gas and the determined first CO2 concentration in the portion of the exhaled gas. In some embodiments, VO2 and/or VCO2 determination may be further based on one or more breathing parameters of the subject. In some embodiments, the one or more breathing parameters may include flow rate of exhaled gas (e.g., determined by the flow sensor included in sensors 21).

In some embodiments, metabolic monitor 16 may be configured to provide information about the metabolic status of the subject based on oxygen consumption (VO2) and carbon dioxide production (VCO2) measurements, and their changes overtime. In some embodiments, VO2 and VCO2 measurements may be used to estimate a subject's energy expenditure (EE) and respiratory quotient (RQ). Energy expenditure (EE) may be used to assess the caloric need of the individual and respiratory quotient (RQ) may provide information on the macronutrient primarily used to produce energy (e.g., carbohydrates, fat, protein, etc.). In some embodiments, metabolic monitor device is a basal metabolic rate (BMR) device, a resting metabolic rate (RMR) device, a resting energy expenditure (REE) device, and/or any device that is capable of providing metabolic rate of the subject.

CO2 monitor 17 is configured to provide information related to CO2 concentration in carbon dioxide production (VCO2) measurements in breathing gas. In some embodiments, CO2 monitor 17 may include one or more sensors (25) configured to output signals related to one or more gas parameters in inhaled and/or exhaled gas by the subject. In some embodiments, sensors 25 may include one or more CO2 concentration sensors (27) configured to output signals related to CO2 concentration in gas exhaled and/or inhaled by the subject (e.g., nondispersive infrared (NDIR) CO2 sensors). In some embodiments, sensors 25 may include a flow rate sensor 29 configured to output signals related to flow rate of inhaled and/or exhaled gas by the subject. In some embodiments, CO2 monitor 17 may include other sensors (e.g., sensors 18 described below). In some embodiments, CO2 monitor 17 may be configured to determine carbon dioxide production (VCO2) based on the CO2 concentration measurements. In some embodiments, VCO2 is further determined based on one or more breathing parameters of the subject (e.g., flow rate of the exhaled gas). In some embodiments, CO2 monitor 17 may be a capnograph. Other CO2 monitors may be considered.

In some embodiments, one or more functions of metabolic monitor 16 and/or CO2 monitor 17 may be assumed by processors 20. In some embodiments, one or more functions of metabolic monitor 16 and/or CO2 monitor 17 may be assumed by processors included in these devices. In some embodiments, one or more functions of metabolic monitor 16 and/or CO2 monitor 17 may be assumed by processors outside of system 10.

Sensor(s) 18 are configured to generate output signals conveying information related to one or more breathing parameters of subject 12. For example, during one or more breaths, during one or more time intervals, and/or continuously. In some embodiments, the one or more breathing parameters may comprise gas parameters related to the breathable gas provided to the subject 12, breathing parameters related to respiration of subject 12, physiological parameters of subject 12, and/or other parameters. The one or more gas parameters of the breathable gas may comprise, for example, one or more of an inhalation flow rate, an exhalation flow rate, inhaled volume, inhaled volume, pressure, humidity, temperature, acceleration, velocity, and/or other parameters of the breathable gas. Breathing parameters related to the respiration of subject 12 may comprise a tidal volume, a timing (e.g., beginning and/or end of inhalation, beginning and/or end of exhalation, etc.), an inhalation flow rate, an exhalation flow rate, a respiration rate, a respiration airflow, a duration (e.g., of inhalation, of exhalation, of a breathing cycle, etc.), respiration frequency, effort of breathing, and/or other breathing parameters. Physiological parameters may include oximetry parameters, pulse, temperature, blood pressure, and/or other physiological parameters. In some embodiments, sensor(s) 18 may comprise one or more sensors that measure such parameters directly (e.g., through fluid communication with the subject and/or the subject interface.) In some embodiments, sensor(s) 18 may comprise one or more sensors that generate output signals related to the one or more parameters indirectly (e.g., through measurements from other sensors or other components within or outside system 10). In some embodiments, sensor(s) 18 may comprise one or more sensors configured to generate output signals related to physiological parameters of subject 12. For example, heart sensor for measuring heart parameters of the subject, motion sensor for detecting subject motion, accelerometer, oximeter, audio sensor, video sensor (camera), and/or other sensors.

Sensor(s) 18 may include sensors disposed in a plurality of locations within or outside system 10. For example, in some embodiments, sensor(s) 18 may be included in metabolic monitor 16 and/or CO2 monitor 17. For example, Sensor(s) 18 may include sensors directly coupled with subject 12, positioned to point at subject 12 (e.g., a camera), and/or in other locations.

Processor 20 is configured to provide information processing capabilities in system 10. As such, processor 20 may include one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may include a plurality of processing units. These processing units may be physically located within the same device (e.g., a server), or processor 20 may represent processing functionality of a plurality of devices operating in coordination (e.g., one or more servers, one or more computing devices 24 associated with users, a medical device, sensor(s) 18, a metabolism monitor, a piece of a hospital equipment, devices that are part of external resources 14, electronic storage 22, and/or other devices.)

As shown in FIG. 1, processor 20 is configured to execute one or more computer program components. The one or more computer program components may comprise one or more of a subject information component 28, a metabolism monitor component 30, CO2 monitor component 32, a correction factor determination component 36, a correction component 38, and/or other components. Processor 20 may be configured to execute components 28, 30, 32, 36, 38 and/or other components by software; hardware; firmware; some combination of software, hardware, and/or firmware; and/or other mechanisms for configuring processing capabilities on processor 20.

It should be appreciated that although components 28, 30, 32, 36, and 38 are illustrated in FIG. 1 as being co-located within a single processing unit, in embodiments in which processor 20 comprises multiple processing units, one or more of components 28, 30, 32, 36, 38, and/or other components may be located remotely from the other components. The description of the functionality provided by the different components 28, 30, 32, 36, 38 and/or other components described below is for illustrative purposes, and is not intended to be limiting, as any of components 28, 30, 32, 36, and/or 38 may provide more or less functionality than is described. For example, one or more of components 28, 30, 32, 36, and/or 38 may be eliminated, and some or all of its functionality may be provided by other components 28, 30, 32, 36, and/or 38. As another example, processor 20 may be configured to execute one or more additional components that may perform some or all of the functionality attributed below to one of components 28, 30, 32, 36, and/or 38.

Subject information component 28, in some embodiments, may be configured to determine (and/or obtain) information related to subject 12. In some embodiments, subject information component 28 may be configured to determine information related to breathing parameters of the subject. In some embodiments, information related to breathing parameters of the subject may be obtained (determined) from metabolic monitor 16, and/or CO2 monitor 17. In some embodiments, breathing parameters information may include one or more of an inhalation flow rate, an exhalation flow rate, inhaled volume, inhaled volume, pressure, humidity, temperature, acceleration, velocity, gas components concentrations (e.g., O2 concentration, CO2 concentration, etc.), and/or other parameters of the breathable gas. Breathing parameters related to the respiration of subject 12 may comprise a tidal volume, a timing (e.g., beginning and/or end of inhalation, beginning and/or end of exhalation, etc.), an inhalation flow rate, an exhalation flow rate, a respiration rate, a respiration airflow, a duration (e.g., of inhalation, of exhalation, of a breathing cycle, etc.), respiration frequency, effort of breathing, exhaled and inhaled gas components concentrations (e.g., O2 concentration, CO2 concentration, etc.), and/or other breathing parameters. In some embodiments, the breathing parameters of the subject may be determined based on output signals from sensor(s) 18.

In some embodiments, information related to subject 12 may include biographical information. For example, biographical information may include demographic information (e.g., gender, ethnicity, age, etc.), vital sign information (e.g., heart rate, temperature, respiration rate, weight, BMI, etc.), medical/health condition information (e.g., a disease type, severity of the disease, stage of the disease, categorization of the disease, symptoms, behaviors, readmission, relapse, etc.), treatment history information (e.g., type of treatments, length of treatment, current and past medications, etc.), and/or other information. In some embodiments, subject information component 28 may include information related to previous breathing parameters (e.g., previous monitoring sessions, and/or previous measurements.)

In some embodiments, subject information component 28 may be configured to determine (and/or obtain) information related to other subjects. For example, subjects with similar breathing parameters information, demographic information, vital sign information, medical/health condition information, treatment history information, and/or other similarities with subject 12. It should be noted that the subject information described above is not intended to be limiting. A large number of information related to subjects may exist and may be used with system 10 in accordance with some embodiments. For example, users may choose to customize system 10 and include any type of subject data they deem relevant. In some embodiments, subject information component 28 may be configured to obtain/extract information from one or more databases (e.g., included in electronic storage 22, external resources 14, one or more medical devices, other internal or external databases, and/or other sources of information.)

Metabolism monitoring component 30 may be configured to obtain information from a metabolism monitor 16. In some embodiments, information from the metabolism monitor may be related to breathing gas parameters. For example, in some embodiments, information from the metabolism monitor may include O2 concentration in exhaled gas by the subject, CO2 concentration in exhaled gas by the subject, O2 consumption (VO2) by the subject, CO2 volume production (VCO2) by the subject, flow rate of inhaled/or exhaled gas, and/or other and/or breathing gas parameters. In some embodiments, In some embodiments, metabolism monitoring component 30 is configured to receive, determine and/or obtain one or more gas parameters (e.g., from components within or outside system 10). The one or more parameters may be determined based on the output signals from sensor(s) 18. In some embodiments, metabolism monitoring component 30 is configured to determine one or more breathing parameters related to respiration of subject 12, one or more parameters of a breathable gas within system 10, (e.g., parameters related to flow of breathable gas delivered by a respiratory device), one or more physiological parameters of subject 12, and/or other parameters. The breathing parameters related to the respiration of subject 12 may comprise beginning and/or end of individual breaths. In some embodiments, the breathing parameters may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiratory airflow, breathing effort, respiration frequency, and/or other breathing parameters. The one or more gas parameters of the flow of breathable gas delivered to the subject may comprise, for example, one or more of a flow rate, heart rate, volume, pressure, humidity, temperature, acceleration, velocity, and/or other gas parameter. Physiological parameters may include oximetry parameters, a pulse, temperature, blood pressure, movement, and/or other physiological parameters.

In some embodiments, metabolism monitoring component 30 is configured to determine flow rate of the exhaled gas based on the output signals from one or more sensor(s) 18. In some embodiments, metabolism monitoring component 30 is configured to determine inhalation flow rate, exhalation flow rate, and/or other gas flow rates within an interface appliance. In some embodiments, the entire exhalation flow rate is determined. In some embodiments, metabolism monitoring component 30 is configured to determine flow rate of a portion of the exhaled gas. For example, in some embodiments, the exhaled gas is sampled (after the overall exhaled gas has been collected). For example, in some embodiments, the sample is a constant proportion of the flow is directed to the mixing chamber for further measurements (e.g., O2 and CO2 concentrations measurements). In some embodiments, metabolism monitoring component 30 is configured to determine volume of air inhaled, and/or volume of air exhaled.

CO2 monitoring component 32 may be configured to obtain information from a CO2 monitor. In some embodiments, information from the CO2 monitor may be related to breathing gas parameters. For example, in some embodiments, information from the CO2 monitor may include CO2 concentration in exhaled gas by the subject, CO2 volume production (VCO2) by the subject, flow rate of inhaled/or exhaled gas and/or other breathing gas parameters.

In some embodiments, CO2 monitoring component 32 may be configured to receive, determine and/or obtain one or more gas parameters (e.g., from components within or outside system 10). In some embodiments, the one or more parameters may be determined based on the output signals from sensor(s) 18. In some embodiments, CO2 monitoring component 32 is configured to determine one or more breathing parameters related to respiration of subject 12, one or more parameters of a breathable gas within system 10, (e.g., parameters related to flow of breathable gas delivered by a respiratory device), one or more physiological parameters of subject 12, and/or other parameters. The breathing parameters related to the respiration of subject 12 may comprise beginning and/or end of individual breaths. In some embodiments, the breathing parameters may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiratory airflow, breathing effort, respiration frequency, and/or other breathing parameters. The one or more gas parameters of the flow of breathable gas delivered to the subject may comprise, for example, one or more of a flow rate, volume, pressure, humidity, temperature, acceleration, velocity, and/or other gas parameter. Physiological parameters may include oximetry parameters, a pulse, temperature, blood pressure, movement, and/or other physiological parameters.

In some embodiments, CO2 monitoring component 32 is configured to determine flow rate of the exhaled gas based on the output signals from one or more sensor(s) 18. In some embodiments, CO2 monitoring component 32 is configured to determine inhalation flow rate, exhalation flow rate, and/or other gas flow rates within an interface appliance. In some embodiments, the entire exhalation flow rate is determined. In some embodiments, CO2 monitoring component 32 is configured to determine flow rate of a portion of the exhaled gas determine one or more breathing gas parameters based on output signals from sensors 18.

Correction factor determination component 36 is configured to receive VO2 and VCO2 information from metabolic monitoring component 30, and VCO2 information from CO2 monitoring component 32. In some embodiments, correction factor determination component 36 is configured to determine a correction factor based on the received VCO2 information from metabolic monitoring component 30, and VCO2 information from CO2 monitoring component 32. Measurements from the CO2 monitor are used to improve the accuracy of the metabolic monitoring measurements of VCO2 and VO2. In some embodiments, the correction factor is applied to the VO2 measurement from the metabolic monitor. This correction may improve the accuracy of this vital sign needed to understand the metabolic demand of the patient.

Figure 2:
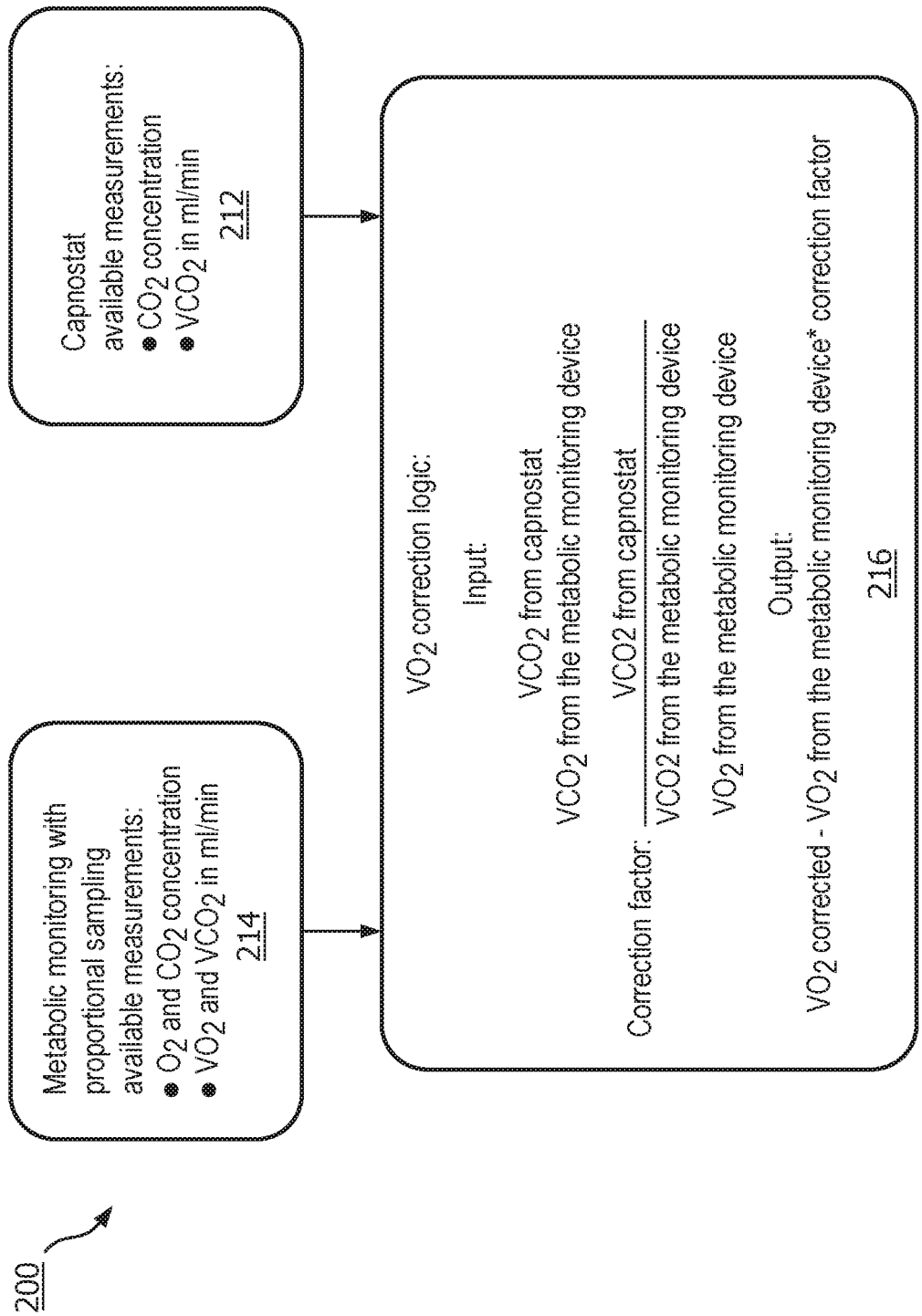
FIG. 2 illustrates a schematic illustration of a model configured to determine metabolic measurements, in accordance with one or more embodiments.

In some embodiments, the correction factor may be computed as the quotient of the VCO2 from the CO2 monitor and the VCO2 from metabolic monitor:

Correction component 38 is configured to receive the determined correction factor from the correction factor determination component 36. In some embodiments, correction component 38 is configured to determine a corrected O2 consumed by the subject VO2 based on the correction factor. In some embodiments, the corrected VO2 is the product of VO2 from the metabolic monitor and the correction factor. VO2 corrected represents the volume per minute of O2 exhaled by the patient in the case the gas analyzed by the metabolic monitor are sampled in an exhalation limb. To compute the VO2 consumed by the patient the corrected measurement from the metabolic monitor is subtracted from the VO2 provided to the patient (e.g., via a ventilator):

FIG. 2 illustrates an example 200 of a model for determining a corrector factor. In some embodiments, model 200 may be executed by one or more components of system 10. In some embodiments, model 200 may be executed by one or more components of processors (20). VCO2 measurements 212 from CO2 monitor (similar to CO2 monitor 17 in FIG. 1) are input into model 216. VO2 and VCO2 measurement 214 from metabolism monitor (similar to metabolism monitor 16 in FIG. 1) are input into model 216. Model 216 is configured to receive VCO2 measurements from the two monitors will be used to compute a correction factor. The correction factor will be applied to the VO2 measurement from the metabolic monitor. the correction factor may be computed as the quotient of the VCO2 from the CO2 monitor and the VCO2 from metabolic monitor. A corrected O2 consumed by the subject VO2 based on the correction factor. In some embodiments, the corrected VO2 is the product of VO2 from the metabolic monitor and the correction factor.

Figure 3:
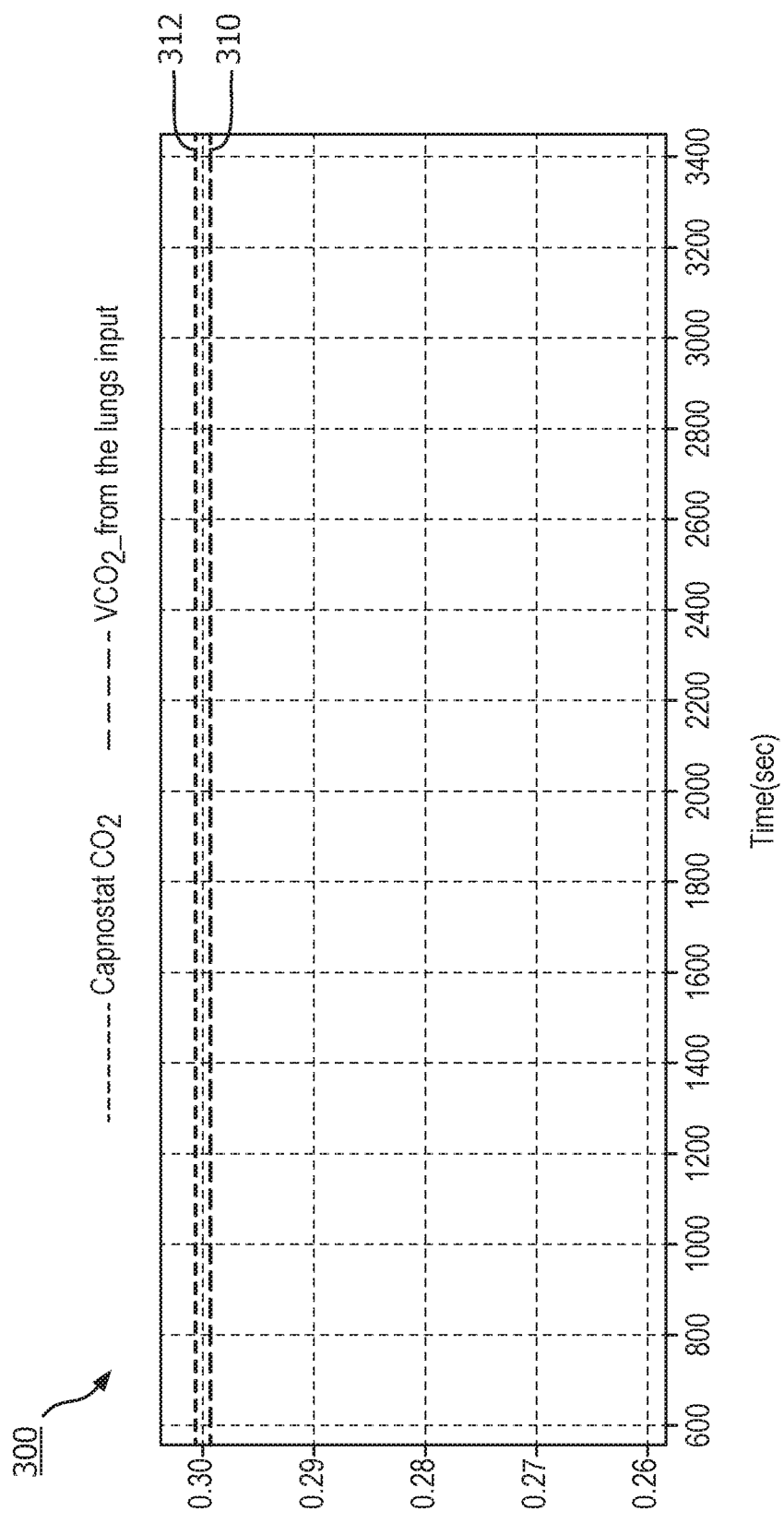
FIG. 3 illustrates an example of plots representing different VCO2 measurements, in accordance with one or more embodiments.
Figure 4:
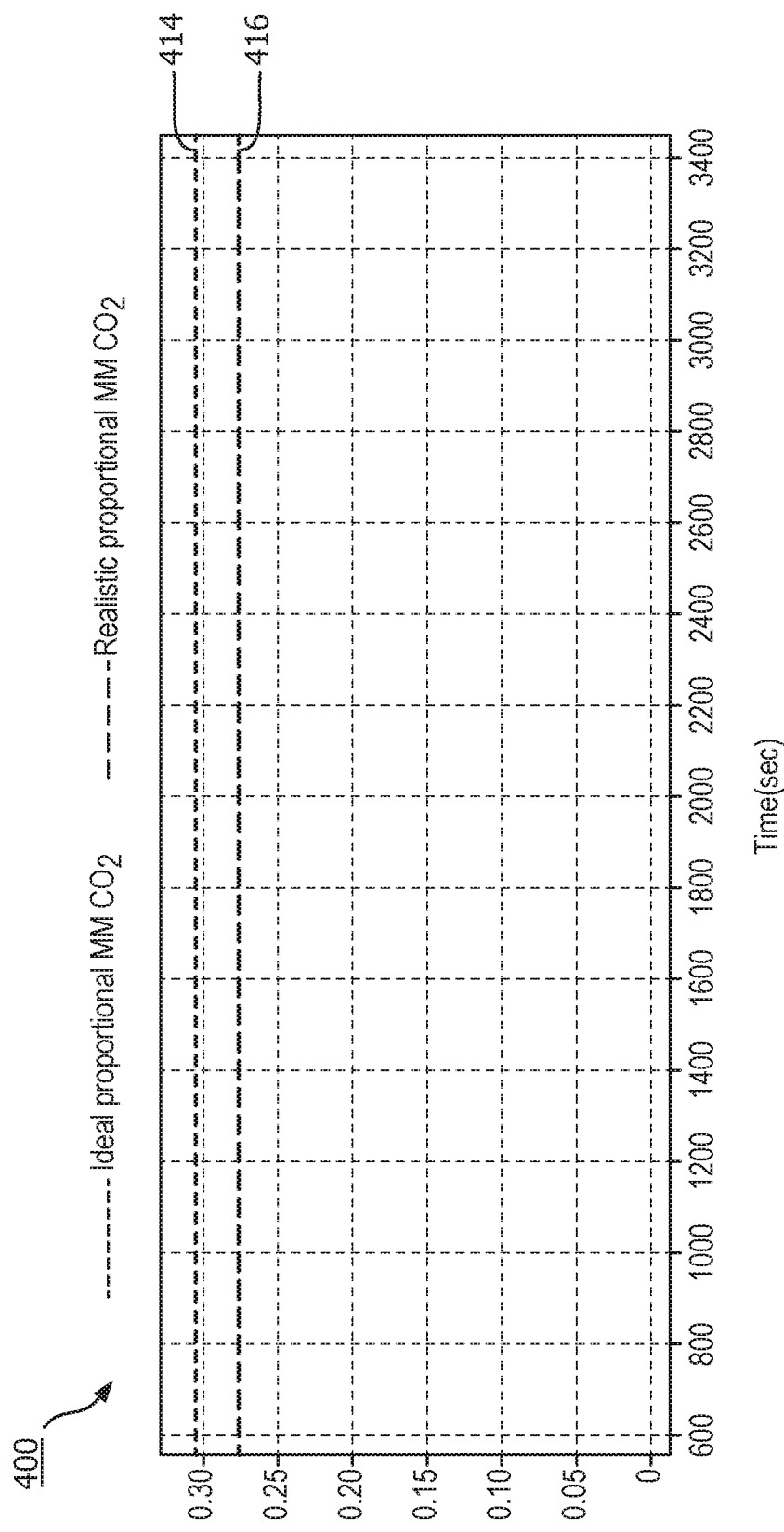
FIG. 4 illustrates an example of plots representing different VCO2 measurements, in accordance with one or more embodiments.

In some embodiments, the correction factor is computed using a model based on a simulation of a patient under mechanical ventilation. In this model, different values of O2 consumption and CO2 production may be simulated. In particular, a simulation of a patient producing 300 ml/min of CO2 and consuming 300 ml/min di O2. FIG. 3 illustrates an example 300 of plots representing VCO2 determined using the simulation model, and VCO2 determined using a CO2 monitor over time. In yellow is the measurement 310 produced by the patient using the simulation model. In green is the measurement 312 from a CO2 monitor (e.g., a capnograph). As can be seen from graph 300, the two measurements are close. FIG. 4 illustrates an example 400 of plots representing VCO2 determined using a metabolic monitoring device using an ideal proportional sampling scheme and VCO2 measurements from the same metabolic monitoring device but with a variable sampling over time. In blue, is the measurements 414 from the metabolic monitor using an ideal proportional sampling scheme over time. In red, is the measurements 416 from the same metabolic monitor but with a sampling that varies from 1.5% to 5% (depending on the amplitude of the subject flow) over time. It is possible to observe, how these two measurements differ for around 10%. This difference determines the correction factor used to correct the VO2 measurement from the metabolic monitor.

Figure 5:
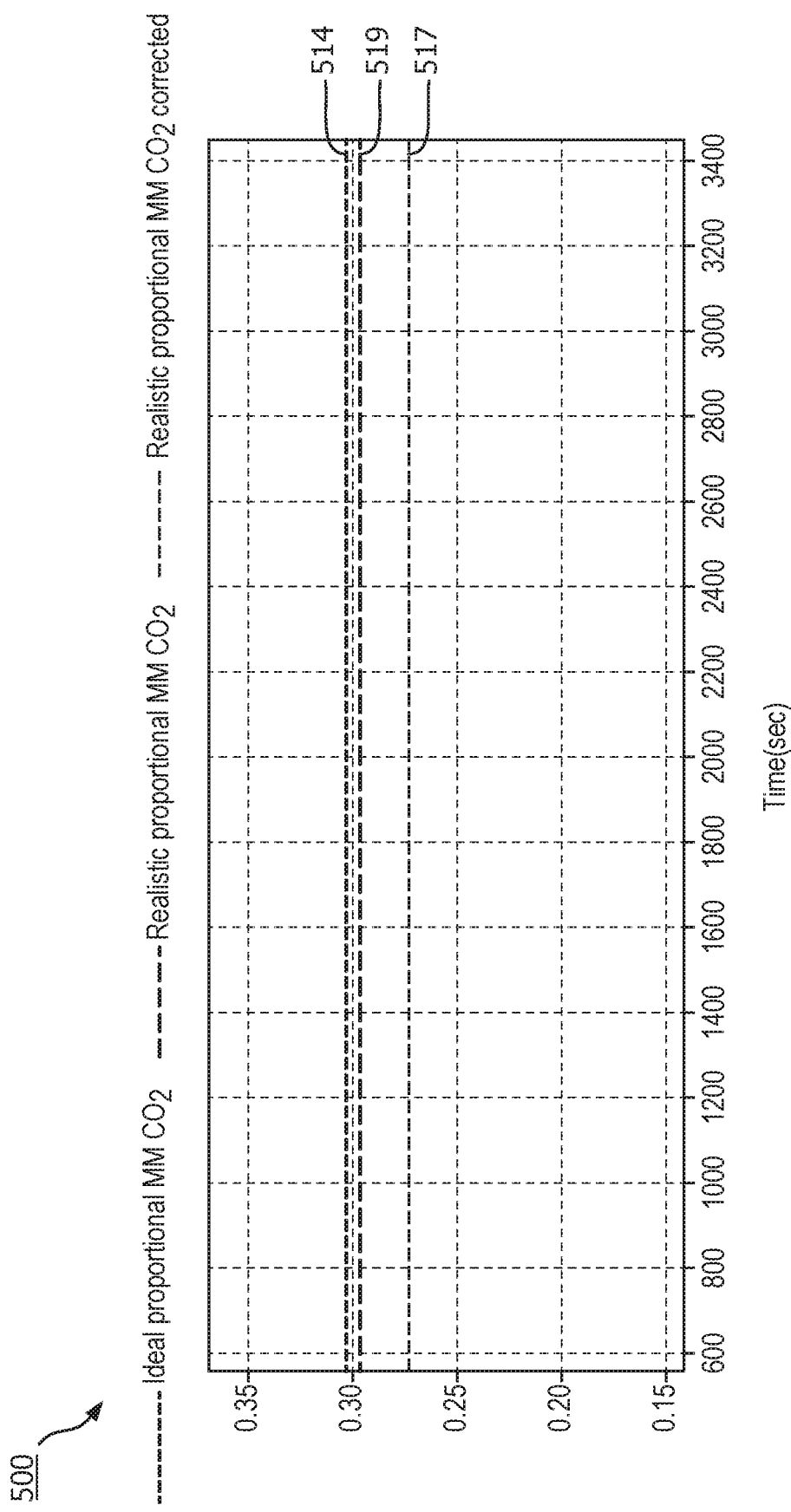
FIG. 5 illustrates an example of plots representing different VO2 measurements, in accordance with one or more embodiments.

In FIG. 5 illustrates an example 500 of plots representing VO2 measurements. In green, is the measurement 515 from the metabolic monitor using the ideal proportional sampling scheme. In light blue, is the measurements 517 from the metabolic monitor with the more realistic sampling. In dark red, is the measurement 519 from the one or more realistic metabolic monitor adjusted with the correction factor. As can be seen from FIG. 5, measurements from the metabolic monitor using a more realistic proportional sampling has an inaccuracy of around 10%. Nevertheless, using the correction factor computed using the VCO2 from the CO2 monitor and VCO2 from the same metabolic monitor reduced the inaccuracy to 0.3%.

Returning to FIG. 1, system 10 may include one or more of external resources 14, electronic storage 22, client computing platform(s) 24, network 26, and/or other components, all being communicatively coupled via a network 26.

External resources 14 include sources of patient and/or other information. In some embodiments, external resources 14 include sources of patient and/or other information, such as databases, websites, etc., external entities participating with system 10 (e.g., a medical records system of a healthcare provider that stores medical history information for populations of patients), one or more servers outside of system 10, a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 14 may be provided by resources included in system 10. External resources 14 may be configured to communicate with processor 20, computing devices 24, electronic storage 22, and/or other components of system 10 via wired and/or wireless connections, via a network (e.g., a local area network and/or the internet), via cellular technology, via Wi-Fi technology, and/or via other resources.

Electronic storage 22 includes electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., computing devices 18, processor 20, etc.). In some embodiments, electronic storage 22 may be located in a server together with processor 20, in a server that is part of external resources 14, in a computing device 24, and/or in other locations. Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via a computing device 24 and/or graphical user interface 40 and/or other external computing systems, information received from external resources 14, sensors 18, and/or other information that enables system 10 to function as described herein.

Client computing platform(s) 24 is configured to provide interfaces between subject 12, caregivers (e.g., doctors, nurses, friends, family members, etc.), patients, and/or other users, and system 10 through which subject 12 and/or other users may provide information to and receive information from system 10. For example, client computing platform(s) 24 may display a representation of the output from metabolic monitor 16, CO2 monitor 17, sensors 18, processors 20, (e.g., a plot, 2D/3D images, video, audio, text, etc.) to a user. This enables data, cues, results, instructions, and/or any other communicable items, collectively referred to as "information," to be communicated between a user (e.g., subject 12, a doctor, a caregiver, and/or other users) and one or more of metabolic monitor 16, CO2 monitor 17, sensors 18, processor 20, electronic storage 22, and/or other components of system 10.

In some embodiments, computing devices 24 may be included in metabolic monitor 16, CO2 monitor 17, sensors 18, processor 20, or in other components of system 10. In some embodiments, individual computing devices 24 maybe included, in desktop computers, laptop computers, tablet computers, smartphones, a wearable device, a medical device, and/or other computing devices associated with subject 12, individual caregivers, patients, and/or other users. In some embodiments, individual computing devices 24 may be included, in equipment used in hospitals, doctor's offices, and/or other medical facilities to patients; test equipment; equipment for treating patients; data entry equipment; and/or other devices.

In some embodiments, computing devices 24 are configured to provide information to, and/or receive information from, the caregivers, patients, and/or other users. For example, computing devices 24 are configured to present a graphical user interface 40 to facilitate display representations of the data analysis, and/or other information. In some embodiments, client computing platform(s) 24 comprises a plurality of separate interfaces. In some embodiments, graphical user interface 40 includes a plurality of separate interfaces associated with computing devices 24, processor 20, metabolic monitor 16, CO2 monitor 17, sensors 18, and/or other components of system 10; multiple views and/or fields configured to convey information to and/or receive information from caregivers, patients, and/or other users; and/or other interfaces.

In some embodiments, computing devices 24 are configured to provide graphical user interface 40, processing capabilities, databases, and/or electronic storage to system 10. As such, computing devices 24 may include processors 20, electronic storage 22, external resources 14, and/or other components of system 10 (e.g., in the same housing). In some embodiments, computing devices 24 are connected to a network (e.g., network 26, the internet, etc.). In some embodiments, computing devices 24 do not include processors 20, electronic storage 22, external resources 14, and/or other components of system 10, but instead communicate with these components via the network. The connection to the network may be wireless or wired. For example, processor 20 may be located in a remote server and may wirelessly cause display of graphical user interface 40 to the caregivers on computing devices 24.

As described above, in some embodiments, an individual computing device 24 is a laptop, a personal computer, a smartphone, a tablet computer, and/or other computing devices. Examples of interface devices suitable for inclusion in an individual computing device 24 include a touch screen, a keypad, touch-sensitive and/or physical buttons, switches, a keyboard, knobs, levers, a display, speakers, a microphone, an indicator light, an audible alarm, a printer, and/or other interface devices. The present disclosure also contemplates that an individual computing device 24 includes a removable storage interface. In this example, information may be loaded into a computing device 24 from removable storage (e.g., a smart card, a flash drive, a removable disk, etc.) that enables the caregivers, patients, and/or other users to customize the implementation of computing devices 24. Other exemplary input devices and techniques adapted for use with computing devices 24 include, but are not limited to, an RS-232 port, an RF link, an IR link, a modem (telephone, cable, etc.), and/or other devices.

The network 26 may include the Internet and/or other networks, such as local area networks, cellular networks, Intranets, near field communication, frequency (RF) link, Bluetooth™, Wi-Fi™, and/or any type(s) of wired or wireless network(s). Such examples are not intended to be limiting, and the scope of this disclosure includes embodiments in which external resources 14, metabolic monitor 16, CO2 monitor 17, sensor(s) 18, processor(s) 20, electronic storage 22, and/or client computing platform(s) 24 are operatively linked via some other communication media.

Figure 6:
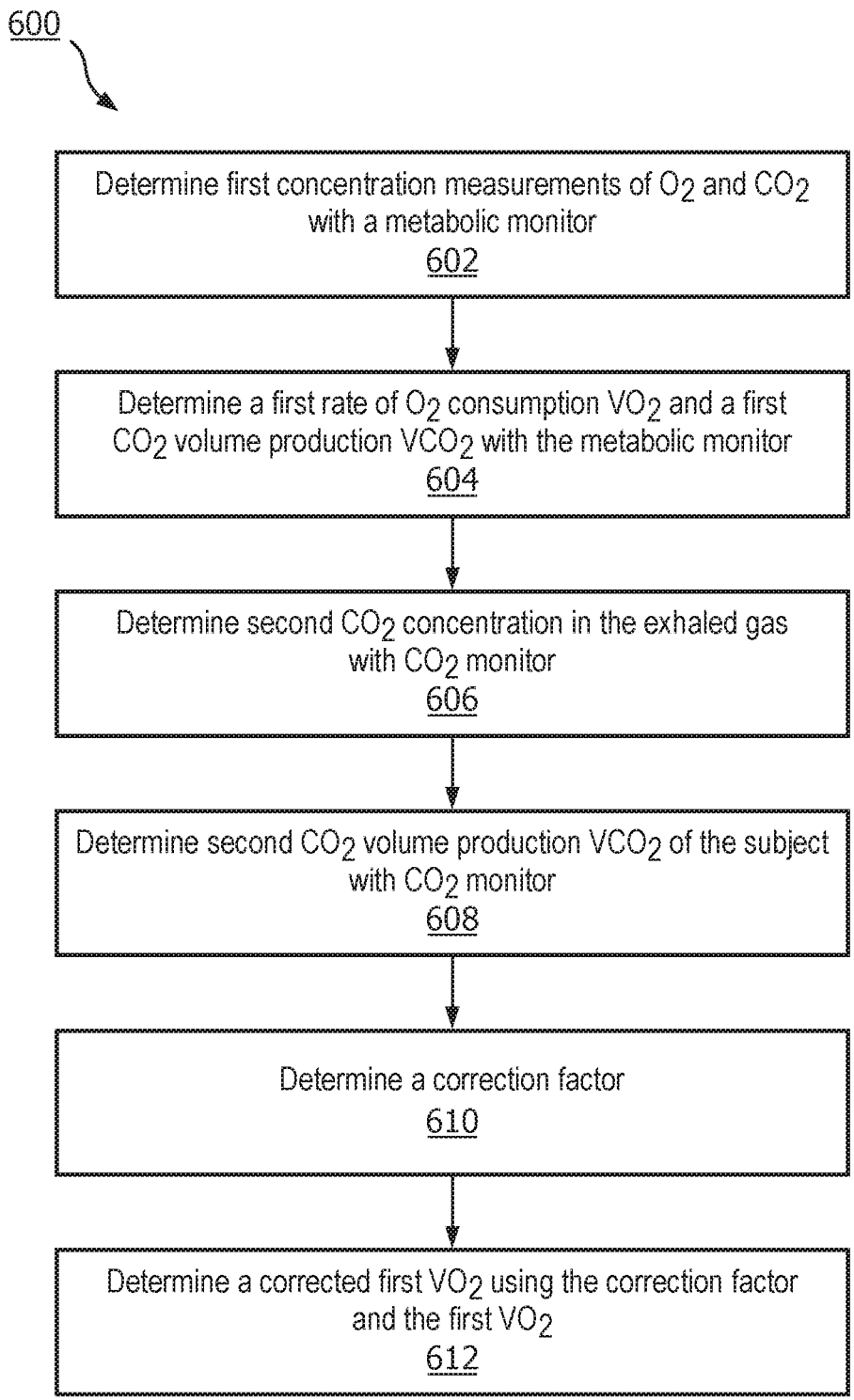
FIG. 6 illustrates a method for determining a correction factor for metabolic measurements, in accordance with one or more embodiments.

FIG. 6 illustrates a method 600 for facilitating prediction of metabolic measurements. The system comprises one or more sensors, one or more physical computer processors, and/or other components. The one or more processors are configured to execute one or more computer program components. The one or more computer program components may comprise a subject information component 28, a sampling component 30, a detection component 32, a prediction component a risk component 36, a control component 38, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, first concentration measurements of O2 and CO2 of a portion of exhaled gas by the subject are determined. In some embodiments, operation 602 is performed by a metabolic monitor, the same as or similar to a metabolic monitor 16, (shown in FIG. 1 and described herein).

At an operation 604, a first rate of O2 consumption VO2 and a first CO2 volume production VCO2 of the subject based on the determined first CO2 concentration of the exhaled gas, and the determined first O2 concentration of the exhaled gas is determined. In some embodiments, operation 604 is performed by a metabolic monitor, the same as or similar to a metabolic monitor 16 (shown in FIG. 1 and described herein).

At an operation 606, second CO2 concentration in the exhaled gas is measured. In some embodiments, operation 606 is performed by a CO2 monitor the same as or similar to a CO2 monitor 17 (shown in FIG. 1 and described herein).

At an operation 608, second CO2 volume production VCO2 of the subject based on the measured CO2 concentration is determined. In some embodiments, operation 608 is performed by a CO2 monitor the same as or similar to a CO2 monitor 17 (shown in FIG. 1 and described herein).

At an operation 610, a correction factor based on the determined first VCO2 and the second VCO2 a correction factor based on the determined first VCO2 and the second VCO2 is determined. In some embodiments, operation 610 is performed by a computer processor component the same as or similar to correction factor determination component 36 (shown in FIG. 1 and described herein).

At an operation 612, a corrected first VO2 using the correction factor and the first VO2 is determined. In some embodiments, operation 612 is performed by a computer processor component the same as or similar to correction component 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for metabolic measurements, the system comprising:
    a metabolic monitor configured to:
        determine first concentration measurements of $O_2$ and $CO_2$ in a portion of gas exhaled by a subject during one or more breaths; and
        determine a first rate of $O_2$ consumption ($VO_2$) and a first $CO_2$ volume production ($VCO_2$) of the subject during the one or more breaths based on the determined first $O_2$ concentration in the portion of the exhaled gas and the determined first $CO_2$ concentration in the portion of the exhaled gas;
    a $CO_2$ monitor configured to:
        determine second $CO_2$ concentration measurements in the gas exhaled by the subject during the one or more breaths; and
        determine second $CO_2$ volume production ($VCO_2$) of the subject during the one or more breaths based on the measured second $CO_2$ concentration; and
    one or more physical computer processors operatively connected the metabolic monitor and the $CO_2$ monitor, the one or more physical computer processors configured by computer readable instructions to:
        determine a correction factor based on the determined first $VCO_2$ and the second $VCO_2$; and
        determine a corrected first $VO_2$ using the correction factor and the first $VO_2$.

2. The system of claim 1, wherein the correction factor is determined as a quotient of the second $VCO_2$ from the $CO_2$ monitor and the first $VCO_2$ from the metabolic monitor.

3. The system of claim 1, wherein the corrected first $VO_2$ is a product of the correction factor and the first $VO_2$.

4. The system of claim 1, wherein the $CO_2$ monitor is a capnograph.

5. The system of claim 1, wherein the one or more physical computer processors are configured to determine a corrected first $VCO_2$ using the correction factor and the determined first $VCO_2$.

6. The system of claim 5, wherein the one or more physical computer processors are configured to determine a metabolic status of the subject based on the corrected first $VO_2$ and the corrected first $VCO_2$.

7. The system of claim 5, wherein the one or more physical computer processors are configured to measure energy expenditure (EE) and/or respiratory quotient (RQ) based on the corrected first $VO_2$ and corrected first $VCO_2$.

8. The system of claim 1, wherein:
the metabolic monitor comprises a plurality of sensors configured to output signals related to one or more breathing parameters of the subject during one or more breaths; and
the one or more physical processors are further configured to determine the first concentration measurements of $O_2$ and $CO_2$ of the portion of the exhaled gas by the subject based on the one or more breathing parameters of the subject.

9. The system of claim 8, wherein the one or more sensors include flow rate sensors configured to measure flow rate of the portion of the exhaled gas in the one or more breaths.

10. The system of claim 1, wherein:
the $CO_2$ monitor comprises a plurality of sensors configured to output signals related to one or more breathing parameters of the subject during one or more breaths; and
the one or more physical processors are further configured to determine the second concentration measurements $CO_2$ in the exhaled gas by the subject based on the one or more breathing parameters of the subject.

11. The system of claim 10, wherein the one or more sensors include flow rate sensors configured to measure flow rate of the exhaled gas in the one or more breaths.

12. The system of claim 1, wherein the metabolic monitor comprises one or more of a $O_2$ sensor, and/or a $CO_2$ sensor.

13. The system of claim 1, wherein the $CO_2$ monitor comprises one or more of a $CO_2$ sensor, and/or flow rate sensor.

14. A method for metabolic measurements, the method comprising:
determining, with a metabolic monitor, first concentration measurements of $O_2$ and $CO_2$ in a portion of gas exhaled by a subject during the one or more breaths;
determining, with the metabolic monitor, a first rate of $O_2$ consumption ($VO_2$) and a first $CO_2$ volume production ($VCO_2$) of the subject during the one or more breaths based on the determined first $O_2$ concentration in the portion of the exhaled gas and the determined first $CO_2$ concentration in the portion of the exhaled gas;

determining, with a $CO_2$ monitor, second $CO_2$ concentration measurements in the gas exhaled by the subject during the one or more breaths;
determining, with the $CO_2$ monitor, second $CO_2$ volume production ($VCO_2$) of the subject during the one or more breaths based on the measured second $CO_2$ concentration;
determining, with one or more physical computer processors ($_2$0), a correction factor based on the determined first $VCO_2$; and the second $VCO_2$; and
determining, with one or more physical computer processors, a corrected first $VO_2$ using the correction factor and the first $VO_2$.

15. The method of claim 14, wherein the correction factor is determined as a quotient of the second $VCO_2$ from the $CO_2$ monitor and the first $VCO_2$ from the metabolic monitor.

16. The method of claim 14, wherein the corrected first $VO_2$ is a product of the correction factor and the first $VO_2$.

17. The method of claim 14, wherein the $CO_2$ monitor is a capnograph configured to continuously measure $CO_2$ concentration in exhaled gas.

18. The method of claim 14, further comprising: determining, with one or more physical computer processors, a corrected first $VCO_2$ using the correction factor and the determined first $VCO_2$.

19. The method of claim 18, further comprising: determining, with one or more physical computer processors, a metabolic status of the subject based on the corrected first $VO_2$ and the corrected first $VCO_2$.

20. The method of claim 18, further comprising: determining, with one or more physical computer processors, energy expenditure (EE) and/or respiratory quotient (RQ) based on the corrected first $VO_2$ and corrected first $VCO_2$.

21. The method of claim 14, further comprising:
providing, with a plurality of sensors in the metabolic monitor, output signals related to one or more breathing parameters of the subject during one or more breaths; and
determining, with one or more processors, the first concentration measurements of $O_2$ and $CO_2$ of the portion of the exhaled gas by the subject based on the output signals from the sensors.

22. The method of claim 21 wherein the one or more sensors include flow rate sensors configured to measure flow rate of the portion of the exhaled gas in the one or more breaths.

23. The method of claim 14, further comprising:
providing, with a plurality of sensors in the $CO_2$ monitor, output signals related to one or more breathing parameters of the subject during one or more breaths; and
determining, with one or more processors, the second concentration measurements $CO_2$ in the exhaled gas by the subject based on the output signals from the sensors.

* * * * *